(12) United States Patent
Heuer et al.

(10) Patent No.: US 7,527,614 B2
(45) Date of Patent: *May 5, 2009

(54) PROTECTIVE TUBE FOR A MEDICATED TAMPON

(75) Inventors: Daniel J. Heuer, Fremont, WI (US); Gregory J. Rajala, Neenah, WI (US); Joyce A. D'Amico, Neenah, WI (US); Steven R. Burnett, West Chester, OH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 311 days.

This patent is subject to a terminal disclaimer.

(21) Appl. No.: 11/090,561

(22) Filed: Mar. 25, 2005

(65) Prior Publication Data

US 2006/0213919 A1 Sep. 28, 2006

(51) Int. Cl.
*A61F 13/15* (2006.01)
*A61F 13/20* (2006.01)
(52) U.S. Cl. .............. 604/385.18; 604/385.17; 604/11; 604/14; 604/15; 604/18
(58) Field of Classification Search ............ 604/385.17, 604/385.18, 904, 11–18
See application file for complete search history.

(56) References Cited

U.S. PATENT DOCUMENTS

| | | |
|---|---|---|
| 639,864 A | 12/1899 | Von Raitz |
| 706,778 A | 8/1902 | Pond |
| 749,220 A | 1/1904 | Pond |
| 812,768 A | 2/1906 | Pond |
| 812,769 A | 2/1906 | Pond |
| 812,770 A | 2/1906 | Pond |
| 1,234,383 A | 7/1917 | Pond |
| 1,395,295 A | 11/1921 | Pond |
| 1,538,678 A | 5/1925 | Blinn |

(Continued)

FOREIGN PATENT DOCUMENTS

DE  2 024 930  12/1971

(Continued)

OTHER PUBLICATIONS

Nagata, Shunji, "Capsule Technology," *Drug Delivery Technology*, vol. 2, No. 2, Mar./Apr. 2002, printed from Internet web page "www.drugdeliverytech.com," 8 pages.

*Primary Examiner*—Jacqueline F. Stephens
(74) *Attorney, Agent, or Firm*—Randall W. Fieldhack; Sebastian C. Pugliese, I; Denise L. Stoker (57) ABSTRACT

A delivery device is provided including a first member having an interior surface, a receiving end, and an insertion end, wherein the insertion end is open; a tampon body positioned within the first member, wherein the tampon body has a proximal tampon body end and a distal tampon body end; and a second member slidably coupled to the interior surface of the first member at the receiving end. The device also includes a dosage form, wherein the dosage form is coupled to the distal tampon body end; and a protective tube including an open attachment end, an open protective tube second end opposite the attachment end, and a protective tube inner surface including an engagement mechanism enabling the protective tube to be coupled to the receiving end of the first member at the attachment end of the protective tube.

30 Claims, 4 Drawing Sheets

U.S. PATENT DOCUMENTS

| | | | |
|---|---|---|---|
| 1,887,526 | A | 11/1932 | Spielberg et al. |
| 2,473,368 | A | 6/1949 | Flintermann |
| 2,696,456 | A | 12/1954 | Hetterick |
| 2,739,593 | A | 3/1956 | Mclaughlin |
| 2,854,978 | A | 10/1958 | Millman et al. |
| 2,922,423 | A | 1/1960 | Rickard et al. |
| 3,086,527 | A | 4/1963 | Forrest |
| 3,415,249 | A | 12/1968 | Sperti |
| 3,515,138 | A | 6/1970 | Hochstrasser et al. |
| 3,521,637 | A | 7/1970 | Waterbury |
| 3,760,808 | A | 9/1973 | Bleuer |
| 3,762,414 | A | 10/1973 | Burnhill |
| 3,791,385 | A | 2/1974 | Davis et al. |
| 3,796,219 | A | 3/1974 | Hanke |
| 3,815,600 | A | 6/1974 | Groves |
| 3,818,911 | A | 6/1974 | Fournier |
| 3,830,237 | A | 8/1974 | Bernardin et al. |
| 3,831,605 | A | 8/1974 | Fournier |
| 3,884,233 | A | 5/1975 | Summey |
| 3,885,564 | A | 5/1975 | Groves |
| 3,902,493 | A | 9/1975 | Baier et al. |
| 3,916,898 | A | 11/1975 | Robinson |
| 3,918,452 | A | 11/1975 | Cornfeld |
| 3,921,636 | A | 11/1975 | Zaffaroni |
| 3,948,254 | A | 4/1976 | Zaffaroni |
| 3,949,752 | A | 4/1976 | Van Stee |
| 3,991,760 | A | 11/1976 | Drobish et al. |
| 3,993,073 | A | 11/1976 | Zaffaroni |
| 3,995,633 | A | 12/1976 | Gougeon |
| 3,995,634 | A | 12/1976 | Drobish |
| 3,995,636 | A | 12/1976 | Murray et al. |
| 4,016,270 | A | 4/1977 | Pharriss et al. |
| 4,077,407 | A | 3/1978 | Theeuwes et al. |
| 4,077,408 | A | 3/1978 | Murray et al. |
| 4,077,409 | A | 3/1978 | Murray et al. |
| 4,159,719 | A | 7/1979 | Haerr |
| 4,160,020 | A | 7/1979 | Ayer et al. |
| 4,160,452 | A | 7/1979 | Theeuwes |
| 4,186,742 | A | 2/1980 | Donald |
| 4,237,888 | A | 12/1980 | Roseman et al. |
| 4,260,570 | A | 4/1981 | Ravel |
| 4,271,835 | A | 6/1981 | Conn et al. |
| 4,286,596 | A | 9/1981 | Rubinstein |
| 4,291,696 | A * | 9/1981 | Ring ............................ 604/14 |
| 4,308,867 | A | 1/1982 | Roseman et al. |
| 4,309,997 | A | 1/1982 | Donald |
| 4,312,348 | A | 1/1982 | Friese |
| 4,317,447 | A | 3/1982 | Williams |
| 4,318,405 | A | 3/1982 | Sneider |
| 4,328,804 | A | 5/1982 | Shimatani |
| 4,340,055 | A | 7/1982 | Sneider |
| 4,341,211 | A | 7/1982 | Kline |
| 4,341,215 | A | 7/1982 | Eldridge |
| 4,373,631 | A | 2/1983 | Friese et al. |
| 4,383,993 | A | 5/1983 | Hussain et al. |
| 4,393,871 | A | 7/1983 | Vorhauer et al. |
| 4,402,695 | A | 9/1983 | Wong |
| 4,405,323 | A | 9/1983 | Auerbach |
| 4,421,504 | A | 12/1983 | Kline |
| 4,439,194 | A | 3/1984 | Harwood et al. |
| 4,483,846 | A | 11/1984 | Koide et al. |
| 4,551,148 | A | 11/1985 | Riley, Jr. et al. |
| 4,553,965 | A | 11/1985 | Conn et al. |
| 4,560,549 | A | 12/1985 | Ritchey |
| 4,582,717 | A | 4/1986 | Von Bittera et al. |
| 4,601,714 | A | 7/1986 | Burnhill |
| 4,610,659 | A | 9/1986 | Friese |
| 4,649,075 | A | 3/1987 | Jost |
| 4,690,671 | A | 9/1987 | Coleman et al. |
| 4,693,705 | A | 9/1987 | Gero |
| 4,795,422 | A | 1/1989 | Conner et al. |
| 4,871,542 | A | 10/1989 | Vilhardt |
| 4,922,928 | A | 5/1990 | Burnhill |
| 4,923,440 | A | 5/1990 | Genaro |
| 4,979,947 | A | 12/1990 | Berman |
| 4,983,393 | A | 1/1991 | Cohen et al. |
| 5,002,540 | A | 3/1991 | Brodman et al. |
| 5,041,080 | A | 8/1991 | Shimatani et al. |
| 5,069,906 | A | 12/1991 | Cohen et al. |
| 5,070,889 | A | 12/1991 | Leveen et al. |
| 5,084,277 | A | 1/1992 | Greco et al. |
| 5,116,619 | A | 5/1992 | Greco et al. |
| 5,201,326 | A | 4/1993 | Kubicki et al. |
| 5,213,566 | A | 5/1993 | Weissenburger |
| 5,273,521 | A | 12/1993 | Peiler et al. |
| 5,295,984 | A | 3/1994 | Contente et al. |
| 5,299,581 | A | 4/1994 | Donnell et al. |
| 5,330,427 | A | 7/1994 | Weissenburger |
| 5,330,761 | A | 7/1994 | Baichwal |
| 5,362,498 | A | 11/1994 | Aiache |
| 5,383,891 | A | 1/1995 | Walker |
| 5,393,528 | A | 2/1995 | Staab |
| 5,417,224 | A | 5/1995 | Petrus et al. |
| 5,466,463 | A | 11/1995 | Ford |
| 5,527,534 | A | 6/1996 | Myhling |
| 5,529,782 | A | 6/1996 | Staab |
| 5,542,914 | A | 8/1996 | Van Iten |
| 5,612,051 | A | 3/1997 | Yue |
| 5,646,206 | A | 7/1997 | Coffin et al. |
| 5,676,647 | A | 10/1997 | Cimber |
| 5,683,358 | A | 11/1997 | Nielsen et al. |
| 5,693,009 | A * | 12/1997 | Fox et al. ............................ 604/14 |
| 5,769,813 | A | 6/1998 | Peiler et al. |
| 5,788,980 | A | 8/1998 | Nabahi |
| 5,840,055 | A | 11/1998 | Sgro |
| 5,912,006 | A | 6/1999 | Bockow et al. |
| 5,958,461 | A | 9/1999 | Larsen |
| 5,988,386 | A | 11/1999 | Morrow |
| 5,993,856 | A | 11/1999 | Ragavan et al. |
| 6,036,666 | A | 3/2000 | Peiler et al. |
| 6,039,968 | A | 3/2000 | Nabahi |
| 6,086,909 | A | 7/2000 | Harrison et al. |
| 6,095,999 | A * | 8/2000 | Jackson et al. ............................ 604/14 |
| 6,096,332 | A | 8/2000 | Yang |
| 6,103,256 | A | 8/2000 | Nabahi |
| 6,126,959 | A | 10/2000 | Levine et al. |
| 6,197,327 | B1 | 3/2001 | Harrison et al. |
| 6,200,288 | B1 | 3/2001 | Heaton et al. |
| 6,203,514 | B1 | 3/2001 | Clifford |
| 6,264,638 | B1 | 7/2001 | Contente |
| 6,264,972 | B1 | 7/2001 | Drury |
| 6,316,019 | B1 | 11/2001 | Yang |
| 6,328,991 | B1 | 12/2001 | Myhling |
| 6,416,778 | B1 | 7/2002 | Ragavan et al. |
| 6,416,779 | B1 | 7/2002 | D'Augustine et al. |
| 6,524,269 | B2 | 2/2003 | Mcnamara |
| 6,526,980 | B1 | 3/2003 | Tracy et al. |
| 6,558,362 | B1 | 5/2003 | Chaffringeon |
| 6,582,389 | B2 | 6/2003 | Buzot |
| 6,592,540 | B2 | 7/2003 | Decarlo |
| 2002/0161088 | A1 | 10/2002 | Kochvar et al. |
| 2002/0193726 | A1 | 12/2002 | Cimber |
| 2003/0028177 | A1 | 2/2003 | Berg et al. |
| 2003/0045829 | A1* | 3/2003 | Gehling et al. ............................ 604/11 |
| 2003/0139709 | A1 | 7/2003 | Gehling |
| 2003/0144639 | A1 | 7/2003 | Gehling |
| 2004/0043061 | A1 | 3/2004 | Leon et al. |
| 2004/0224008 | A1 | 11/2004 | Zhang |
| 2006/0213918 | A1 | 9/2006 | Rajala et al. |
| 2006/0216334 | A1 | 9/2006 | Gehling et al. |

| | | | |
|---|---|---|---|
| 2006/0217652 A1 | 9/2006 | Heuer et al. | |

FOREIGN PATENT DOCUMENTS

| | | |
|---|---|---|
| DE | 2 146 092 | 3/1973 |
| DE | 2 309 575 A | 9/1974 |
| DE | 3 248 152 A1 | 6/1984 |
| EP | 0 110 793 B1 | 3/1987 |
| EP | 0 747 045 A2 | 12/1996 |
| EP | 0 962 201 A1 | 12/1999 |
| GB | 2 277 447 A | 11/1994 |
| JP | 02-212431 A | 8/1990 |
| JP | 07-000450 A | 1/1995 |
| WO | WO 79/00014 A1 | 1/1979 |
| WO | WO 82/02489 A1 | 8/1982 |
| WO | WO 82/04185 A1 | 12/1982 |
| WO | WO 87/02576 A1 | 5/1987 |
| WO | WO 94/08536 A1 | 4/1994 |
| WO | WO 97/19680 A1 | 6/1997 |
| WO | WO 97/45066 A1 | 12/1997 |
| WO | WO 99/47121 A1 | 9/1999 |
| WO | WO 99/48453 A1 | 9/1999 |
| WO | WO 00/66213 A1 | 11/2000 |
| WO | WO 01/13836 A1 | 3/2001 |
| WO | WO 01/80937 A1 | 11/2001 |
| WO | WO 02/03896 A1 | 1/2002 |
| WO | WO 02/09631 A1 | 2/2002 |
| WO | WO 02/051718 A1 | 7/2002 |
| WO | WO 03/007862 A2 | 1/2003 |
| WO | WO 03/020240 A2 | 3/2003 |
| WO | WO 03/037381 A1 | 5/2003 |
| WO | WO 03/059318 A2 | 7/2003 |
| WO | WO 2006/104631 A1 | 10/2006 |

* cited by examiner

PROTECTIVE TUBE FOR A MEDICATED TAMPON

BACKGROUND

This invention pertains to delivery devices used for the application of various therapeutic treatments or other non-medicinal preparations into the vaginal or other cavity and methods of providing such devices.

Many disease states and physiological conditions may occur in a woman, including symptoms associated with premenstrual syndrome, menstruation, and menopause. These symptoms may include dysmenorrhea (menstrual cramping), irritability, water retention, moodiness, depression, anxiety, skin changes, headaches, breast tenderness, tension, weight gain, cravings, fatigue, hot flashes, itching and other associated sensory maladies.

Many of these symptoms are due to changes in hormonal levels throughout the menstrual cycle. One example that affects a large number of post-pubescent women is dysmenorrhea, which is the occurrence of painful uterine cramps during menstruation. Menstrual cramping is associated with increased levels of prostaglandin F2α, prostaglandin E2, and, in some cases, leukotrienes in the endometrium and menstrual fluid. These eicosinoids lead to restricted blood flow to the uterus and increased uterine contractions, causing pain.

Various analgesics may be effective in limiting the pain from dysmenorrhea; however some orally-delivered analgesics can cause nausea and vomiting or other untoward side effect therefore alternative routes of analgesic delivery are of interest.

Attempts have been made to deliver analgesics in the vicinity of the cervix and the vaginal mucosa using various vaginally-inserted devices and methods. Because many of these symptoms typically occur in conjunction with menstruation, some have tried to combine an analgesic with a tampon by coating the tampon, dipping the tampon, or by combining the analgesic with the tampon materials.

For example, in a method of preparation of such a product appropriate for a laboratory setting, a formulation of a fatty compound excipient and an analgesic are heated to a liquid state. Constant mixing of the heated formulation is required to produce a homogeneous formulation. The formulation is then poured onto the tip of a tampon held in a form to contain the liquid. As the formulation cools, the ingredients solidify into a solid waxy substance that has adhered to the absorbent material of the tampon and is thereby securely fastened to the tip of the tampon.

SUMMARY OF THE INVENTION

Several problems are inherent in a process that attempts to introduce a formulation including a therapeutic agent into or onto a tampon by coating, dipping, solidifying, or the like. Processes such as these may work in a laboratory setting but may not be feasible within an automated tampon manufacturing process. Because of dosing requirements, the formulation including a therapeutic agent must be maintained in a solution that is both homogeneous and of the proper purity to ensure consistent concentration of the therapeutic agent. These requirements are difficult to accomplish during production operation of an automated tampon manufacturing process, and are significantly more difficult to maintain when the automated tampon manufacturing process stops. In addition, different styles and sizes of tampons may have different densities and will absorb an applied liquid formulation including a therapeutic agent differently, resulting in variability in the abilities of the tampons to release the therapeutic agent.

Specifically, the need to provide constant agitation or mixing of the formulation including a therapeutic agent poses challenges as to how to keep a therapeutic agent homogeneously suspended in a solution when the automated tampon manufacturing process stops. The use of inline mixers and recirculation of the heated liquid formulation during machine stops may provide a method to keep the formulation moving and mixed. However, because a machine could be stopped for several hours, the stability of some formulation mixtures may be compromised by long durations at elevated temperatures, or by mechanical shear forces due to the continuous pumping of the recirculating liquid.

The present invention solves these problems by coupling a pre-manufactured dosage form to a tampon to form a medicated tampon. The dosage form, which includes a therapeutic agent, is solid or semi-solid at room temperature, is sufficiently stable, and may be manufactured separately in a controlled facility, whereby the dose of the therapeutic agent is easily controlled through controls on homogeneity, concentration, and purity.

The advantages of using a pre-manufactured dosage form over an in-line process where the medicated ingredients are applied to the tampon coincident with the tampon manufacturing process are numerous. The dosage form would be desirably produced at a pharmaceutical manufacturer whose manufacturing facility meets current regulatory and quality requirements for drugs and/or devices as appropriate. This could ensure that a therapeutic agent with the correct dose and purity is dispersed within the dosage form. The use of separately-manufactured dosage forms in this manner simplifies the modifications to an existing tampon manufacturing process. The use of separately-manufactured dosage forms in this manner also allows multiple types of therapeutic agents to be applied to the tampon. The chemical and physical stabilities of the dosage form are not compromised by the final assembly process onto the tampon. The final assembly process is less dependent on the physical characteristics of the absorbent structure of the tampon, because only a partial phase change of the dosage form at the attachment juncture may be required to bond the dosage form with the tampon absorbent body.

More specifically, the present invention provides a delivery device including a first member having an interior surface, a receiving end, and an insertion end, wherein the insertion end is open; a tampon body positioned within the first member, wherein the tampon body has a proximal tampon body end and a distal tampon body end; and a second member slidably coupled to the interior surface of the first member at the receiving end. The device also includes a dosage form, wherein the dosage form is coupled to the distal tampon body end; and a protective tube including an open attachment end, an open protective tube second end opposite the attachment end, and a protective tube inner surface including an engagement mechanism enabling the protective tube to be coupled to the receiving end of the first member at the attachment end of the protective tube.

In another aspect, the present invention relates to a method for producing a delivery device, the method including producing a tampon assembly having a first member having an interior surface, a receiving end, and an insertion end, wherein the insertion end is open and has a circular radial cross section; and a tampon body positioned within the first member, wherein the tampon body has a proximal end and a distal end. The tampon assembly also includes a second member slidably coupled to the interior surface of the first member at the receiving end; and a retaining ridge within the first member adjacent to the insertion end. The method also includes attaching a dosage form to the distal end of the tampon body; and coupling to the first member a protective tube including an attachment end, an open protective tube second end opposite the attachment end, and a protective tube inner surface including an engagement mechanism enabling the protective tube to be coupled to the first member at the receiving end such that the protective tube encloses the dosage form.

In another aspect, the present invention relates to a method for providing a therapeutic agent to a consumer, the method including manufacturing a plurality of tampon assemblies, each including a tampon having a tampon body; manufacturing a plurality of dosage forms; coupling one of the dosage forms to one of the tampon bodies and a protective tube to the associated tampon assembly to form a medicated tampon assembly; and packaging together a tampon assembly and a medicated tampon assembly to allow a consumer to choose whether to use the tampon assembly or the medicated tampon assembly.

In another aspect, the present invention relates to a method for providing a therapeutic agent to a consumer, the method including packaging together a tampon assembly and a medicated tampon assembly to allow a consumer to choose whether to use the tampon assembly or the medicated tampon assembly; and instructing the consumer in how to determine which of the tampon assembly or the medicated tampon assembly to use.

In another aspect, the present invention provides a device including a first member having an interior surface, a receiving end, and an insertion end, wherein the insertion end is open; and a tampon body positioned within the first member. The device also includes a second member slidably coupled to the interior surface of the first member at the receiving end; and a protective tube including an open attachment end, an open protective tube second end opposite the attachment end, and a protective tube inner surface including an engagement mechanism enabling the protective tube to be coupled to the receiving end of the first member at the attachment end of the protective tube.

The present invention relates to a therapeutic agent delivery system that is integral with or associated with a feminine care product. The therapeutic agent delivery system including the therapeutic agent and excipients may include any therapeutic agent that may be absorbed into the body through the vaginal or other epithelium, or deposited topically on the vaginal or other epithelium, for the purposes of treating a physiological disease, state, or condition.

Other objects and advantages of the present invention will become more apparent to those skilled in the art in view of the following description and the accompanying drawings.

DETAILED DESCRIPTION OF THE PREFERRED EMBODIMENTS

The invention as described herein will be described for exemplary purposes using a tampon as an example of a feminine care product. The invention, however, applies equally to other forms of products, including tampon-like devices and vaginally-inserted devices, and should not be limited to the example described herein. In addition, although the example described includes a tampon with absorbent material, a product without absorbent material, such as a tampon applicator or other similar applicator, is also contemplated within the invention. Also contemplated is the use of the present invention in conjunction with non-catamenial feminine products such as incontinence products, including female incontinence inserts.

The term "surface" and its plural generally refer herein to the outer or the topmost boundary of an object.

The term "dosage form" is used herein as a generic term for a unit form of a formulation that includes a therapeutic agent. The dosage form includes a discrete and consistent quantity of the therapeutic agent to allow for consistent dosing of one receiving the dosage form. The dosage form may be a suppository, a capsule, a tablet, a gel, or any other suitable form. The dosage form may also be spherical, ovoid, domal, generally flat, or any other suitable shape dictated by the needs of the application of the dosage form. The dosage form may have convex, concave, planar, arcuate, or any other suitable surfaces as dictated by the needs of the application of the dosage form.

Figure 1:
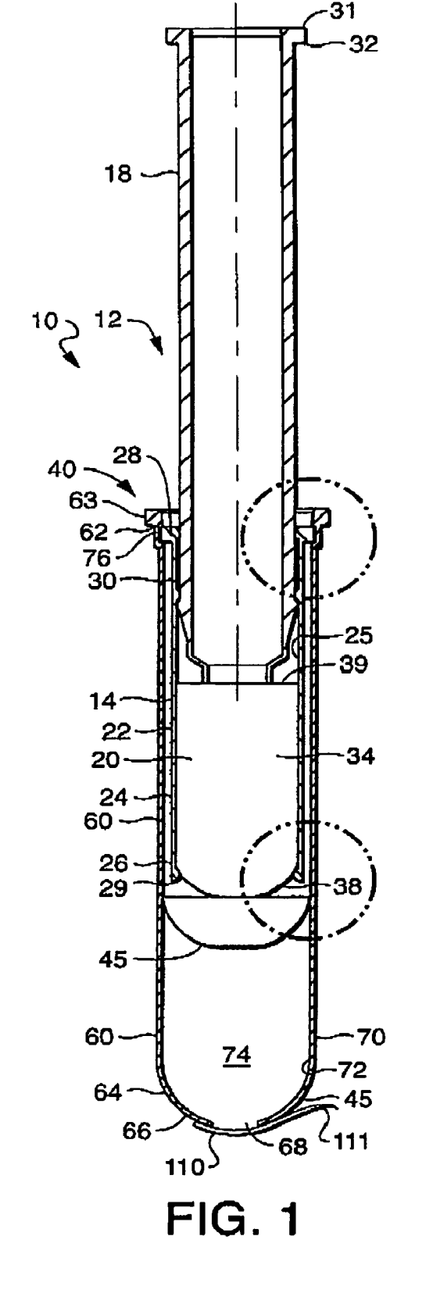
FIG. 1 is a cross-sectional elevation view of a medicated tampon assembly of the present invention.

FIG. 1 illustrates a delivery device in the form of a medicated tampon assembly 10 that includes a tampon assembly 40 and a protective tube 60. The tampon assembly 40 includes a tampon applicator 12 with a first member 14 and a second member 18, where the tampon applicator 12 is designed to house a catamenial tampon 20. The protective tube 60 is designed to attach to the first member 14, as is described in more detail below. In another aspect of the present invention, the tampon assembly 40 or the tampon applicator 12 may be referred to simply as an applicator, particularly if the tampon assembly 40 does not include a tampon 20, or if the tampon applicator 12 is not associated with a tampon 20.

The tampon applicator 12 includes a first member 14 that may be in the form of a spirally wound, convolutely wound or longitudinally seamed hollow tube which is formed from paper, paperboard, cardboard, plastic, other suitable material, or a combination of such materials. Any plastic in the first member 14 is preferably polyethylene, but may be polypropylene or other suitable plastic. The first member 14, also commonly referred to as an outer tube, may be of any suitable dimensions necessary to house a particular size of tampon 20. The first member 14 has a wall 22 with an outside or exterior surface 24 and an inner or interior surface 25.

The first member 14 is sized and configured to house the tampon 20, and should have a substantially smooth exterior surface 24 to facilitate insertion of the first member 14 into a woman's vagina, should the tampon applicator 12 be used alone. When the exterior surface 24 is smooth and/or slippery, the first member 14 will easily slide into a woman's vagina without subjecting the internal tissues of the vagina to abrasion. The first member 14 may be coated to give it a high slip characteristic. Wax, polyethylene, a combination of wax and polyethylene, cellophane and clay are representative coatings that may be applied to the first member 14 to facilitate comfortable insertion. The first member 14 itself may be formulated to give it a high slip characteristic, including the addition of additives to the resin from which the first member is made, or by an alteration in physical structure of the exterior surface 24, such as adding pebbling or other bumps, to decrease the amount of surface area in contact with the vaginal or other epithelium.

Figure 3:
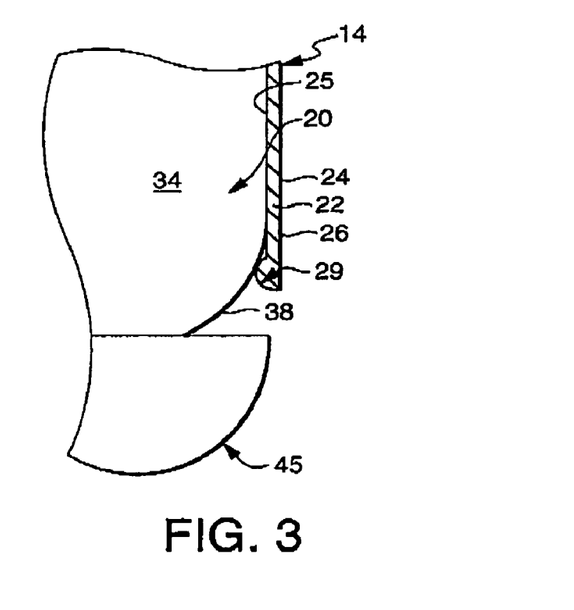
FIG. 3 is an expanded cross-sectional elevation view of a retaining ridge to be used in conjunction with the medicated tampon assembly of FIG. 1.

The first member 14 has an insertion end 26 and a receiving end 30. The insertion end 26 is open such that the insertion end 26 has an opening of a diameter approximately equal to the diameter of the first member 14. As best shown in FIG. 3, the first member 14 also includes a circumferential retaining ridge 29 positioned within the first member 14 adjacent the insertion end 26. The retaining ridge may also be spaced apart from the insertion end 26 (not shown) to allow additional room for a dosage form 45. The retaining ridge 29 projects inwardly from the interior surface 25 within the first member 14. The retaining ridge 29 may extend completely around the interior surface 25, or may be segmented to extend partially around the interior surface 25. The retaining ridge 29 assists in retaining the tampon 20 within the first member 14 during manufacturing, shipping, and handling. FIG. 3 shows the tampon 20 partially extending beyond the retaining ridge 29 and the insertion end 26 to facilitate attachment of a dosage form 45 to the tampon 20, as described in more detail below. The tampon 20 may also be positioned (not shown) entirely within the first member 14 to provide additional protection to the dosage form 45.

Figure 2:
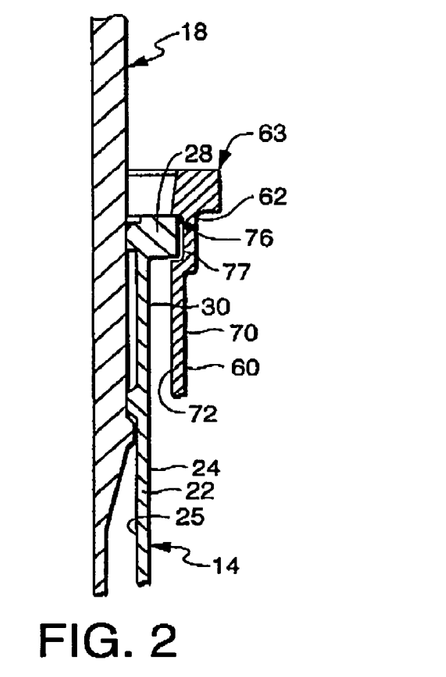
FIG. 2 is an expanded cross-sectional view of an engagement mechanism to be used in conjunction with the medicated tampon assembly of FIG. 1.

Referring to FIGS. 1 and 2, the receiving end 30 of the first member 14 has part of an engagement mechanism 76 (described in more detail below) to facilitate attachment of the protective tube 60 to the first member 14.

Returning to FIG. 1, and as stated above, the medicated tampon assembly 10 includes a second member 18, also commonly referred to as an inner tube. The second member 18, like the first member 14, may be a spirally wound, a convolutely wound or a longitudinally seamed hollow tube constructed from paper, paperboard, cardboard, plastic, other suitable material, or a combination of these materials. The second member 18 may be constructed of the same material as the first member 14 or it may be made out of a different material. The second member 18 may also be a solid stick or use some other unique shape. It is also possible to form a finger flange 32 on the free end 31 of the second member 18 to provide an enlarged surface onto which the user's forefinger may rest. The finger flange 32 thereby functions as a seat for the forefinger and facilitates movement of the second member 18 into the first member 14. The first member 14 may have a fingergrip ring 28 located proximate the receiving end 30. The fingergrip ring 28 provides an enlarged surface onto which one or more fingers of the user may rest. In use, the user may position one or more fingers on the fingergrip ring 28 and one or more fingers on the finger flange 32. The user then holds the fingergrip ring 28 and pushes the finger flange 32 to move the second member 18 toward and into the first member 14.

A tampon 20 is an absorbent member primarily designed to be worn by a woman during her menstrual period to absorb menses and other body fluids. The tampon 20 includes a tampon body 34 and a withdrawal string (not shown). The tampon body 34 is normally compressed into the form of a cylinder and may have a blunt, rounded or shaped forward end. The tampon body 34 has a forward or distal end 38 that is closer to the cervix when the tampon 20 is in use. The tampon body 34 also has a proximal end 39 that is closer to the vaginal opening when the tampon 20 is in use. The tampon 20 commonly has a withdrawal string fastened to the tampon body 34 and extending from the proximal end 39. The withdrawal string serves as a means for withdrawing the tampon 20 from the woman's vagina. Catamenial tampons suitable for use in the present invention include an absorbent material as is known in the art. The distal end 38 of the tampon body 34 or the tampon body 34 itself may be formed into specific shapes such as various cup shapes to enhance the therapeutic agent contact area with the cervix, anterior fornix, posterior fornix, lateral fornices, vaginal epithelium areas, or conformance to other anatomical areas within the vaginal or other cavity.

The medicated tampon assembly 10 includes a dosage form 45. In one aspect of the present invention, the dosage form 45 may be produced in any suitable form including, but not limited to, tablets, capsules, suppositories, gels, disks, lozenges, films, coatings, and other forms. In an alternate aspect of the present invention, the dosage form 45 may be produced in encapsulated form.

In another aspect of the present invention, the tablet, suppository, or capsule may be designed to melt at approximately body temperature, or to dissolve or otherwise disperse in the presence of a sufficient aqueous or other liquid trigger, or appropriate chemistry, such as a suitable pH.

In an additional aspect of the present invention, the dosage form 45 may be formed in any shape to promote contact with anatomical structures such as the vaginal epithelium, the anterior fornix, the posterior fornix, lateral fornices, the cervix, or other structures.

The dosage form 45 may include any therapeutic agent, along with any excipients, compounds, or other ingredients that are desirable to introduce into the vaginal or other cavity to promote the functionality of that therapeutic agent. The excipients may assist the release of the therapeutic agent, or assist in the absorbency of the therapeutic agent into the vaginal or other epithelium. The use of excipients to facilitate the formulation, delivery, stability, and aesthetic properties of a therapeutic agent delivery system is well known to those familiar with the art. Examples of ingredients that may accompany the therapeutic agent in the dosage form 45 include excipients, biologically-compatible adhesives, surfactants, and penetration enhancers. An example of a suitable excipient is SUPPOCIRE suppository base, available from Gattefossé Corp. SUPPOCIRE suppository base is a semi-synthetic glyceride. An example of a suitable biologically-compatible adhesive is hydroxypropyl methylcellulose (HPMC), available as METHOCEL* K15M from The Dow Chemical Company. An example of a suitable surfactant is polysorbate 80, available from Spectrum Chemical Manufacturing Corp. An example of a suitable penetration enhancer is LABRAFIL M 1944 C nonionic amphiphilic excipient, available from Gattefossé Corp.

For the purposes of this invention, any therapeutic agent that will treat the vaginal or other cavity, other mucosal tissue, or will be absorbed into a user's body through the vaginal or other epithelium for the purposes of treating diseases or conditions, promoting the growth of normal vaginal bacterial flora, or promoting vaginal health may be used. Examples of therapeutic agents include but are not limited to vitamins, minerals, hormones, moisturizers, antifungal agents, antibacterial agents, pro-biotics, botanicals, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

Some therapeutic agents for use in this invention are absorbable through the vaginal or other epithelium and travel to the uterus by a unique portal of veins and arteries that are known to exist between the vagina, the cervix, and the uterus. This anastomosis eliminates first-pass metabolism by the liver, effectively delivering higher concentrations of the therapeutic agent to the uterus than would otherwise be available via oral dosing. Those of skill in the art know the efficacy of various therapeutic agents when introduced at a particular anatomical location. For example, when the therapeutic agent is selected to treat dysmenorrhea, it preferably is selected from the following group: nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

Alternatively therapeutic agents modify the vaginal or other environment to enhance the wellness of this anatomical region. The benefits may be rather simple, for example increasing comfort by providing moisturization and/or lubricity. These benefits may also be more complex, for example modulating epithelial cell function to address vaginal atrophy. The beneficial therapeutic agents may reduce negative sensations such as stinging, burning, itching, etc, or introduce positive sensations to improve comfort.

Additionally, the dosage form 45 may be combined with any absorbent tampon design. The dosage form 45 is preferably positioned at the distal end 38 of the tampon body 34. In alternate aspects of the present invention, the dosage form 45 may be positioned at the proximal or string end 39 of the tampon body 34, or any other suitable position between the distal and proximal ends 38, 39 of the tampon body 34. The dosage form 45 may be designed to partially cover the absorbent structure on the tip of the tampon or fully cover the tampon tip.

In other aspects of this invention, the distal end 38 of the tampon body 34 or the tampon body 34 itself may be formed into specific shapes such as various cup shapes to enhance the therapeutic agent contact area with the cervix, posterior fornix, anterior fornix, lateral fornices, vaginal epithelium areas, or conformance to other anatomical areas within the vaginal or other cavity. The tampon body 34 may include a recess, a dimple, a depression, a concavity, or a reservoir (generically a recess, not shown) at the distal end 38 (see FIG. 1), at the proximal end 39, or at any point between the distal and proximal ends 38, 39. The recess is designed to accommodate the dosage form 45. The dosage form 45 may be applied to the recess by any method described herein or by any other suitable method. In an alternate aspect of the present invention, the recess may be formed as a simple dimple. In other alternate aspects of the present invention, the distal end 38 of the tampon body 34 may flat, convex, or of any other suitable shape or arrangement.

The dosage form 45 may be coupled to a tampon body 34 by any method described herein. In one method of coupling the dosage form 45 to the tampon body 34, a portion of the dosage form 45 is heated to melt all or some of that portion of the dosage form 45. Such heating may be accomplished using heated air, heated liquid, infrared, or any other suitable heating means. The dosage form 45 is then abutted with the tampon body 34 such that the melted region of the portion is applied with appropriate pressure to engage the tampon body 34. The melted region of the portion then re-solidifies, becoming attached to the tampon body 34. In one aspect of the present invention, the dosage form 45 is thereby mechanically engaged with the fibers of the tampon body 34. In a different aspect of the present invention, the tampon body 34 may be heated and then put in contact with the dosage form 45, thus using the heat from the tampon body 34 to heat and melt at least part of the dosage form 45.

In a different aspect of the present invention, the dosage form 45 is at least partially coated with a suitable biologically-compatible adhesive such as HPMC or other suitable adhesive and then abutted with the tampon body 34 such that the dosage form 45 is affixed to the tampon body 34. The HPMC may be applied alternatively or additionally to one of the tampon body 34 or the dosage form 45.

In a different aspect of the present invention, the attachment may be accomplished in a manufacturing environment by introducing a small amount of heated, melted excipient such as SUPPOCIRE suppository base onto the distal end 38 of the tampon body 34 just prior to introducing the dosage form 45 onto the distal end 38. The heat contained in the melted excipient partially melts the dosage form 45 and creates a secure bond when both the dosage form 45 and the introduced excipient cool and harden. The heated excipient may be applied alternatively or additionally to the dosage form 45.

Figure 6:
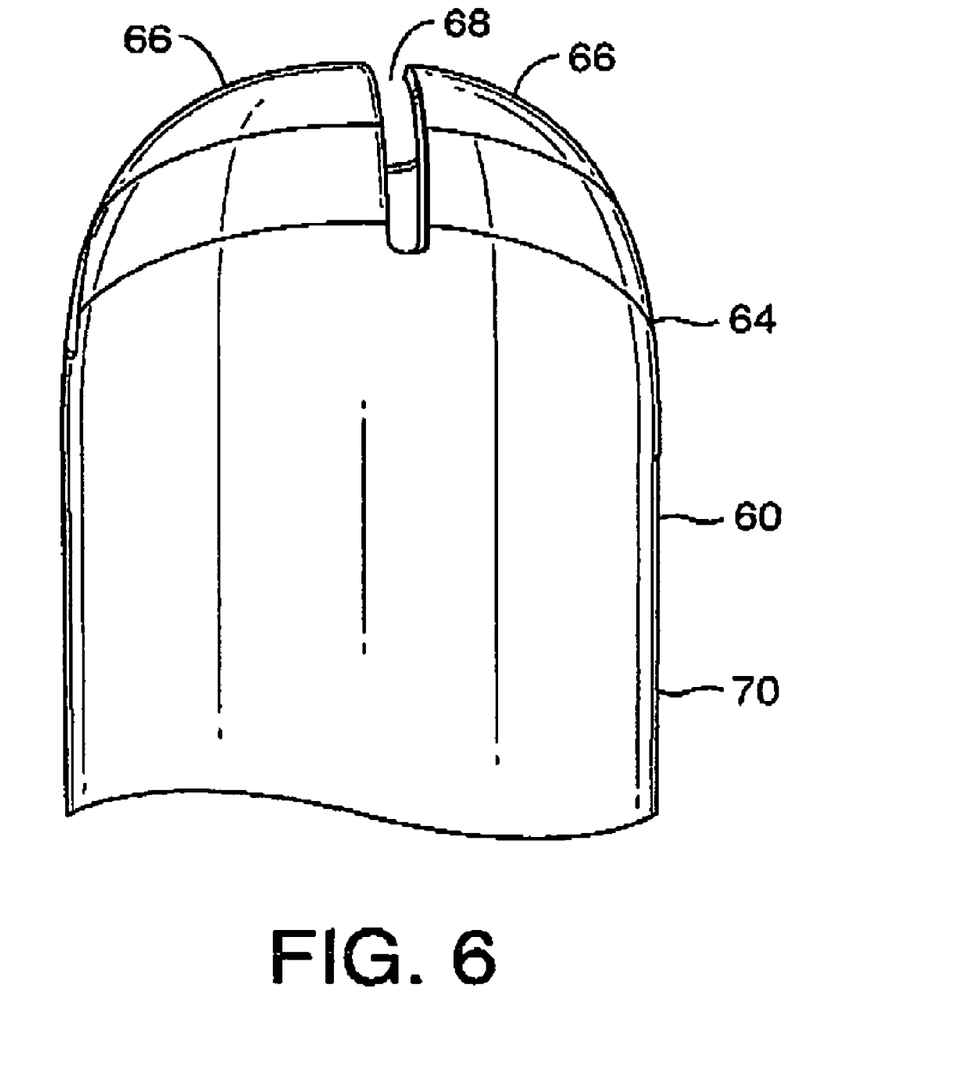
FIG. 6 is a partial perspective view of a protective tube for the medicated tampon assembly of FIG. 1.
Figure 7:
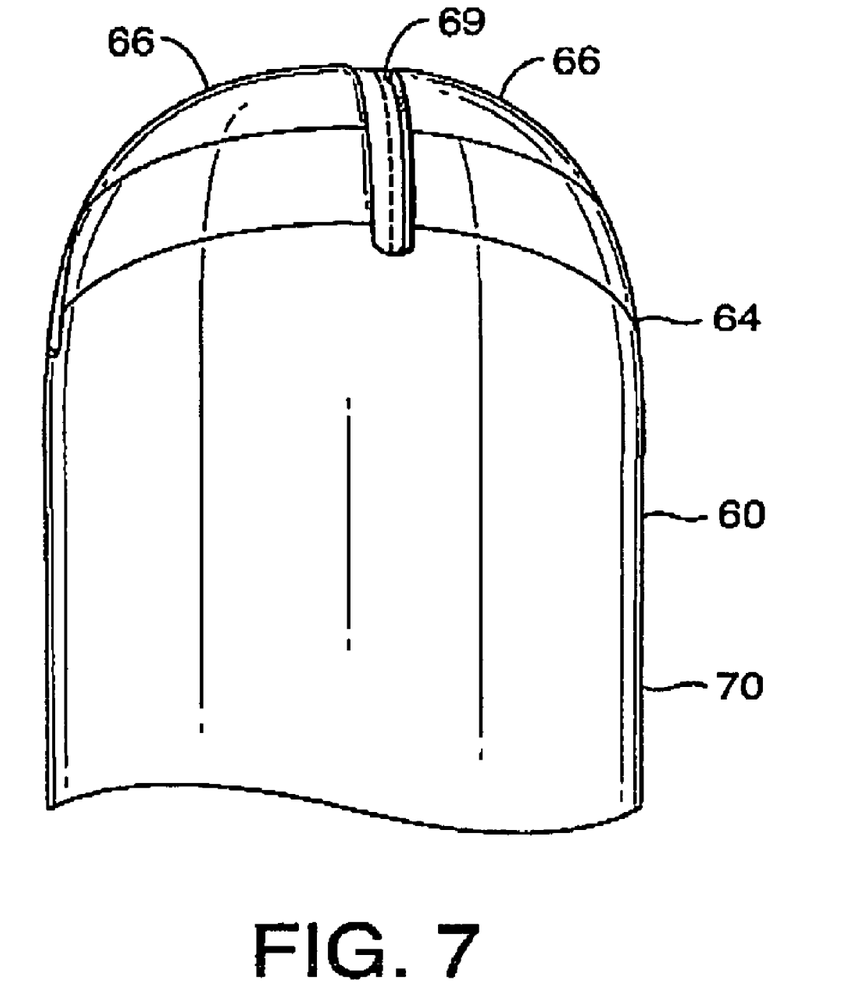
FIG. 7 is a partial perspective view of another aspect of a protective tube for the medicated tampon assembly of FIG. 1.

Referring to FIG. 1, the medicated tampon assembly 10 also includes the protective tube 60. The protective tube 60 includes an attachment end 62 and a protective tube second end 64. The protective tube 60 may have a protective tube ring 63 at the attachment end 62. As shown in FIG. 6, the protective tube 60 may include a plurality of pleats or petals 66 at the protective tube second end 64 that may radially open such that the protective tube second end 64 of the protective tube 60 has a diameter approximately equal to the diameter of the protective tube 60. The petals 66 may be either even or odd in number and may be equally spaced apart or non-uniformly arranged. Between any two petals 66 is a gap 68 that provides additional flexibility to the petals 66. As shown in FIG. 7, and in another aspect of the present invention, the gaps 68 may be filled by a frangible portion 69 such that the protective tube second end 64 is closed by petals 66 and frangible portions 69 until force applied by the dosage form 45, the tampon 20, or the second member 18 causes the frangible portions 69 to break, allowing the petals 66 to open.

The protective tube 60 also includes a protective tube outer surface 70 and a protective tube inner surface 72, where the protective tube inner surface 72 defines and at least partially encloses a protective tube cavity 74. The protective tube 60 is preferably manufactured from material similar to that of the first member 14, but any suitable material may be used. The protective tube 60 may be manufactured with a large protective tube cavity 74, as shown in FIG. 1, to accommodate growth in the tampon 20. The protective tube 60 may also be manufactured with a smaller protective tube cavity 74 (not shown) for a more compact medicated tampon assembly 10.

The protective tube 60 is sized and configured to house the first member 14, and the protective tube outer surface 70 should be substantially smooth to facilitate insertion of the protective tube 60 into a woman's vagina. When the protective tube outer surface 70 is smooth and/or slippery, the protective tube 60 will easily slide into a woman's vagina without subjecting the internal tissues of the vagina to abrasion. The protective tube 60 may be coated to give it a high slip characteristic. Wax, polyethylene, a combination of wax and polyethylene, cellophane and clay are representative coatings that may be applied to the protective tube 60 to facilitate comfortable insertion. The protective tube 60 itself may be formulated to give it a high slip characteristic, including the addition of additives to the resin from which the first member is made, or by an alteration in physical structure of the protective tube outer surface 70, such as adding pebbling or other bumps, to decrease the amount of surface area in contact with the vaginal or other epithelium.

The attachment end 62 of the protective tube 60 includes an engagement mechanism 76 (shown in FIGS. 2, 4, and 5) that allows the protective tube 60 to be attached to the first member 14 with minimal force. The attachment provided by the engagement mechanism 76 is preferably one-way or permanent for the improved structural integrity of the protective tube 60 with the first member 14 in use. In most types of engagement mechanisms suitably applied in such an application, the engagement mechanism 76 typically includes a first portion 77 and a second portion 78, where the first portion 77 engages with the second portion 78 to complete the engagement mechanism 76. The first portion 77 is positioned on one of the protective tube 60 or the first member 14, and the second member 78 is positioned on the other of the protective tube 60 or the first member 14. The engagement mechanism 76 may be any suitable mechanism, including, but not limited, to a snap ring, conventional screw threads, quarter-turn threads, a mechanical latch, and an escapement-type mechanism.

The engagement mechanism 76 between the protective tube 60 and the first member 14 are shown in FIG. 2 as having a snap-on engagement profile. Such a profile is convenient to manufacture, may be assembled with minimal force, and creates the one-way attachment preferred for the structural integrity of this product. In one aspect of an engagement mechanism 76 of the present invention, the protective tube 60 is designed to engage with the fingergrip ring 28 of the first member 14, as shown in FIG. 2. The protective tube 60 includes an indent 75 that snaps around and accommodates the fingergrip ring 28. The engagement mechanism 76 may be configured to provide an audible click and a tactile sensation to signal that the protective tube 60 is properly in place with respect to the first member 14.

Figure 4:
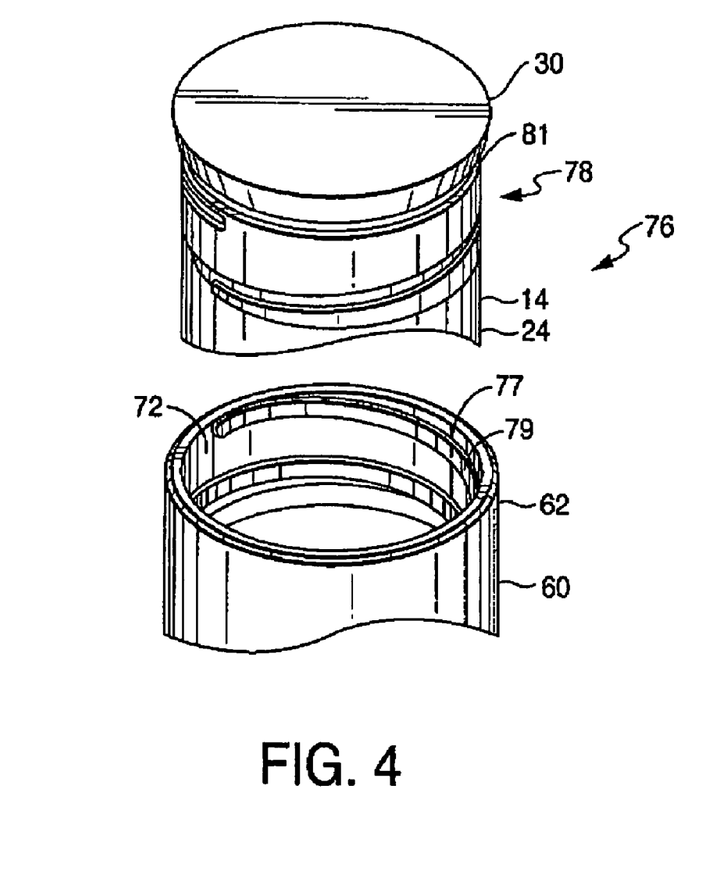
FIG. 4 is a partial perspective view of another aspect of an engagement mechanism for the medicated tampon assembly of FIG. 1.

In an example of a screw-type engagement mechanism 76 illustrated in FIG. 4, the protective tube 60 includes a first portion 77 including helically-positioned projections 79, and the first member 14 includes a second portion 78 including helically-positioned projection-receiving spaces 81. The protective tube 60 is moved toward and twisted onto the first member 14 such that the helically-positioned projections 79 engage or interlock with the projection-receiving spaces 81. In another aspect of this example (not shown), the first portion 77 including helically-positioned projections 79 is positioned on the first member 14, and the second portion 78 including helically-positioned projection-receiving spaces 81 is positioned on the protective tube 60.

Figure 5:
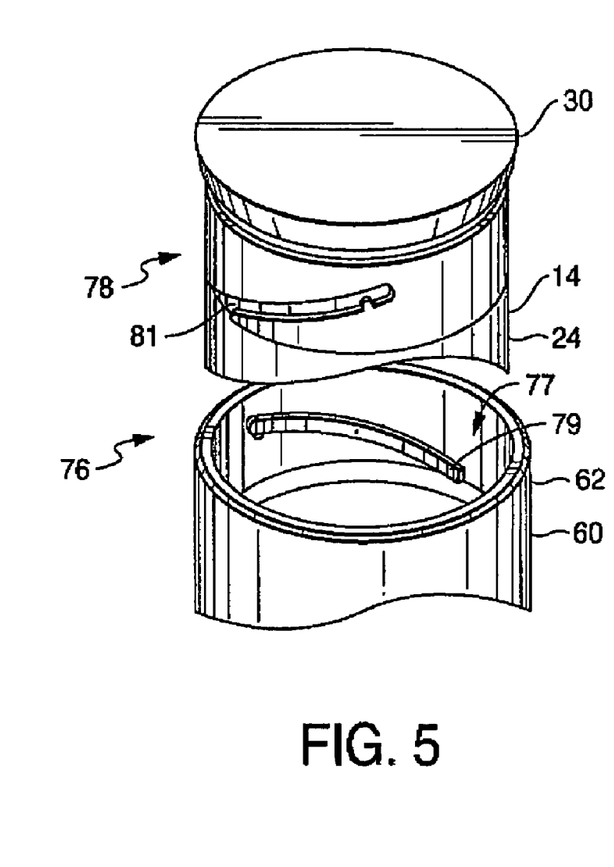
FIG. 5 is a partial perspective view of another aspect of an engagement mechanism for the medicated tampon assembly of FIG. 1.

In an example of a quarter-turn-type engagement mechanism 76 illustrated in FIG. 5, the protective tube 60 includes a first portion 77 including a helically-positioned projection 79, and the first member 14 includes a second portion 78 including a helically-positioned projection-receiving space 81. The protective tube 60 is moved toward and twisted onto the first member 14 such that the helically-positioned projection 79 engages or interlocks with the projection-receiving space 81. In another aspect of this example (not shown), the first portion 77 including a helically-positioned projection 79 is positioned on the first member 14, and the second portion 78 including a helically-positioned projection-receiving space 81 is positioned on the protective tube 60.

In another aspect of the present invention, the engagement mechanism 76 may include an aligning mechanism (not shown) to ensure that the protective tube 60 is particularly aligned, as desirable, with the first member 14 when the two are combined to form the medicated tampon assembly 10. The aligning mechanism may be a keyway or any other suitable aligning mechanism.

Referring to FIG. 1, the protective tube 60 may also include a containment seal 110 to seal the dosage form 45 within the protective tube cavity 74. The containment seal 110 is removable using pull tab 111.

The containment seal 110 may be positioned at the protective tube second end 64 of the protective tube 60 such that the containment seal 110 extends sufficiently to seal the gaps 68. The containment seal 110 is affixed to the protective tube 60 at the protective tube second end 64 using any suitable adhesive or affixing means, including the use of hot-melt, water-based, solvent-based, or pressure-sensitive adhesives, mucilage, a thermal seal, ultrasonic bonding, pressure, friction, electrostatics, cling-like poly wraps, or surface energy effects. The containment seal 110 remains affixed during shipping and handling, but may be removed by a manufacturer or a consumer to reveal the contents of the protective tube 60. The containment seal 110 may be durable or may melt or dissolve in the body. The containment seal 110 may be formed from any suitable material, including foil, poly, film, film laminates, nonwovens, nonwoven laminates, protective materials such as TYVEK protective material, and any suitable elastomeric substance including rubber, or by a combination of these materials that do not adversely interact with the dosage form. The containment seal 110 may also be configured to tear along perforations or frangible sections under pressure, allowing the dosage form 45 and a tampon 20 to be expelled.

The dosage form 45, protective tube 60, and the tampon assembly 40 are combined to form the medicated tampon assembly 10. A protective tube 60 is axially aligned with a tampon assembly 40 including a dosage form 45. The protective tube 60 and the tampon assembly 40 are moved toward each other using minimal force to cause the engagement mechanism of the protective tube 60 and the first member 14 to engage, resulting in the protective tube 60 becoming permanently attached to the first member 14. The containment seal 110 may be applied to the protective tube second end 64 of the protective tube 60. The medicated tampon assembly 10 may then be packaged and shipped.

More specifically, the various components of the medicated tampon assembly 10 may be manufactured and assembled in a variety of ways, but generally focus on three subassemblies: the tampon assembly 40, the protective tube 60, and the dosage form 45.

The dosage form 45 may be produced by the same manufacturer as the manufacturer of the tampon assembly 40. The dosage form 45 may also be produced by a separate manufacturer and provided to the tampon manufacturer in any suitable manner. As an example, a dosage form manufacturer with a facility specifically designed for pharmaceutical manufacturing that meets current regulatory and quality requirements for drugs and/or devices, as appropriate, may produce the dosage forms 45 under conditions such that homogeneity, concentration, and purity of the dosage form 45 are closely controlled, and such that production is in accordance with applicable regulations. The dosage form 45 may then be sealed and shipped to the manufacturer of the tampon assembly 40. In this manner, the dosage form 45 is produced by a manufacturer with appropriate experience, and the tampon manufacturer may be relieved of establishing a pharmaceutical-production facility. This process is described in more detail in co-pending U.S. patent application Ser. No. 10/335,816 filed on Dec. 31, 2002 and titled "Medicated Tampon".

In another aspect of the present invention, the tampon assembly 40 may be produced by a manufacturer different from the manufacturer of the protective tube 60 and both assemblies (40, 60) may be shipped to the manufacturer of the dosage form 45 for manufacture of the medicated tampon assembly 10. In another aspect of the present invention, the medicated tampon assembly 10 is produced by a manufacturer different from the manufacturer of the dosage form 45, the manufacturer of the tampon assembly 40, and the manufacturer of the protective tube 60.

In any case, the dosage form 45, the protective tube 60, and the tampon assembly 40 are each manufactured. The dosage form 45 and the tampon assembly 40 are combined and sealed if appropriate, and then the protective tube 60 is combined with the tampon assembly 40/dosage form 45 combination by a manufacturer.

Packaging the medicated tampon assembly 10 may include instructions for use of the medicated tampon assembly 10. Such instructions may include information regarding when a medicated tampon assembly 10 is appropriate to use and standard pharmaceutical information regarding the dosage form 45 and therapeutic agent(s) contained in the dosage form 45.

In another aspect of the present invention, the marketing and packaging of the devices described herein may be tailored to the needs of a woman's menstrual cycle. Recognizing that a medicated tampon assembly 10 may be required by a woman on only a limited basis, a tampon assembly 40 and a medicated tampon assembly 10, or a plurality of one or each of these, may be provided to a consumer, either in the same or separate packaging. The packaging of the medicated tampon assembly 10, the tampon assembly 40, or both may include instructions concerning use of a tampon assembly 40, or a medicated tampon assembly 10, or both, including which type of tampon should be used, and how and when it should be used. The tampon assembly 40 and the medicated tampon assembly 10 may be provided by the same vendor, or may be acquired by the consumer from different vendors. Alternatively, the consumer may also be provided with a dosage form 45, either in the same or separate packaging, to be used as one might use a suppository. In this case, the consumer could also be provided with instructions to help determine which of the tampon assembly 40, the medicated tampon assembly 10, or the dosage form 45 to use, and how and when to use each of these.

In another aspect of the present invention, the protective tube 60 may be used without a dosage form 45 present and in conjunction with a tampon assembly 40 that does not have a petal-type closure mechanism at the insertion end 26 of the first member 14 to assist in the insertion of such a tampon assembly 40. The structure employed in such a use will closely resemble that of the medicated tampon assembly 10, except that no dosage form 45 will be included.

In use, and referring to FIG. 1, the consumer is instructed to remove the medicated tampon assembly 10 from its packaging. The consumer may be instructed to remove the containment seal 110 from the medicated tampon assembly 10 and use the medicated tampon assembly 10 as one would use a standard tampon. The medicated tampon assembly 10 functions because the second member 18 is telescopically movable relative to the first member 14. As the second member 18 is pushed into the first member 14, the tampon 20 with the dosage form 45 is thereby forced against the protective tube petals 66. The contact by the dosage form 45 causes the protective tube petals 66 to radially open to a diameter that is sufficient to allow the dosage form 45 and the tampon 20 to be expelled from the first member 14. With the dosage form 45 and the tampon 20 properly positioned in the woman's vaginal or other cavity, the tampon applicator 12 with the attached protective tube 60 are withdrawn and properly discarded.

Once the tampon 20 is properly positioned in the woman's vaginal or other cavity, the tampon body 34 absorbs menses and other bodily fluids, and the dosage form 45 delivers the therapeutic agent to the vaginal or other epithelium for local or topical therapeutic action or from there, the therapeutic agent may be transferred to the uterus by normal bodily functions to relieve the condition to be treated.

The invention has been described with reference to various specific and illustrative aspects and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. A delivery device comprising:
   a first member having an interior surface, a receiving end, and an insertion end, wherein the insertion end is open;
   a tampon body positioned within the first member, wherein the tampon body has a proximal tampon body end and a distal tampon body end;
   a second member disposed within the receiving end of the first member, such that the second member is telescopically movable with respect to the first member;
   a dosage form, wherein the dosage form is coupled to the tampon body; and
   a protective tube comprising
      an attachment end,
      an open protective tube second end opposite the attachment end, and
         a protective tube inner surface including an engagement mechanism enabling the protective tube to be coupled to the receiving end of the first member at the attachment end of the protective tube.

2. The device of claim 1, further comprising a retaining ridge within the first member adjacent to the insertion end.

3. The device of claim 2, wherein the retaining ridge projects inwardly from the interior surface of the first member.

4. The device of claim 1, the first member further comprising a fingergrip ring adjacent the receiving end.

5. The device of claim 4, wherein the engagement mechanism is adapted to engage the fingergrip ring.

6. The device of claim 1, wherein the engagement mechanism is selected from a snap ring, a screw mechanism, quarter-turn threads, a mechanical latch, an adhesive, a melting process, a welding process, and an escapement-type mechanism.

7. The device of claim 1, wherein the engagement mechanism has a first portion and a second portion, wherein one of the protective tube and the receiving end includes the first portion of the engagement mechanism, and the other of the protective tube and the receiving end includes the second portion of the engagement mechanism.

8. The device of claim 1, wherein the protective tube is affixed to the first member.

9. The device of claim 1 wherein the protective tube second end is at least partially closed by a plurality of flexible petals.

10. The device of claim 9, wherein the flexible petals have gaps therebetween, and further comprising a containment seal coupled to the protective tube second end and sealing the gaps.

11. The device of claim 10, wherein the containment seal is removable.

12. The device of claim 9, wherein the flexible petals have frangible portions therebetween.

13. The device of claim 1, wherein the dosage form is affixed to the distal end of the tampon body.

14. The device of claim 13, further comprising a bioadhesive affixing the dosage form to the distal end of the tampon body.

15. The device of claim 13, wherein the dosage form is affixed to the distal end of the tampon body using heat.

16. A method for producing a device, the method comprising:
producing a tampon assembly having
a first member having an interior surface, a receiving end, and an insertion end, wherein the insertion end is open and has a circular radial cross section; and
a tampon body positioned within the first member, wherein the tampon body has a proximal end and a distal end;
attaching a dosage form to the distal end; and
coupling to the first member a protective tube comprising
an attachment end,
an open protective tube second end opposite the attachment end, and
a protective tube inner surface including an engagement mechanism enabling the protective tube to be coupled to the first member at the receiving end such that the protective tube encloses the dosage form.

17. The method of claim 16, wherein the producing act is performed at a first facility and the attaching act is performed at a second facility.

18. The method of claim 16, further comprising shipping the tampon assembly from a first facility to a second facility prior to the attaching act.

19. The method of claim 16, wherein the protective tube second end is at partially closed by a plurality of flexible petals.

20. The method of claim 19, wherein the flexible petals have frangible portions therebetween.

21. The method of claim 16, wherein the coupling act includes affixing the protective tube to the first member.

22. The method of claim 16, the first member further comprising a retaining ridge within the first member adjacent to the insertion end.

23. A device comprising:
a first member having an interior surface, a receiving end, and an insertion end, wherein the insertion end is open;
a tampon body positioned within the first member;
a second member disposed within the receiving end of the first member, such that the
second member is telescopically movable with respect to the first member; and
a protective tube comprising
an open attachment end,
an open protective tube second end opposite the attachment end, and
a protective tube inner surface including an engagement mechanism enabling the protective tube to be coupled to the receiving end of the first member at the attachment end of the protective tube.

24. The device of claim 23, further comprising a retaining ridge within the first member adjacent to the insertion end.

25. The device of claim 24, wherein the retaining ridge projects inwardly from the interior surface of the first member.

26. The device of claim 23, further comprising a fingergrip ring affixed to the first member adjacent the receiving end.

27. The device of claim 23, wherein the protective tube second end is at least partially closed by a plurality of flexible petals.

28. The device of claim 23, wherein the engagement mechanism is adapted to engage the fingergrip ring.

29. The device of claim 23, wherein the engagement mechanism is selected from a snap ring, a screw mechanism, quarter-turn threads, a mechanical latch, an adhesive, a melting process, a welding process, and an escapement-type mechanism.

30. The device of claim 23, wherein the protective tube is affixed to the first member.

* * * * *